United States Patent
Reine et al.

(10) Patent No.: US 7,902,377 B2
(45) Date of Patent: Mar. 8, 2011

(54) METHOD FOR PREPARING MEDETOMIDINE AND ITS SALTS

(75) Inventors: Inese Reine, Riga (LV); Armands Zandersons, Riga (LV)

(73) Assignee: JSC Grindeks, Riga (LV)

( * ) Notice: Subject to any disclaimer, the term of this patent is extended or adjusted under 35 U.S.C. 154(b) by 0 days.

(21) Appl. No.: 12/312,324

(22) PCT Filed: Nov. 2, 2007

(86) PCT No.: PCT/EP2007/061822
§ 371 (c)(1),
(2), (4) Date: May 5, 2009

(87) PCT Pub. No.: WO2008/055852
PCT Pub. Date: May 15, 2008

(65) Prior Publication Data
US 2010/0048915 A1 Feb. 25, 2010

(30) Foreign Application Priority Data
Nov. 6, 2006 (EP) .................................... 06123548

(51) Int. Cl.
*A61K 31/4164* (2006.01)
*C07D 233/56* (2006.01)
(52) U.S. Cl. .................................... 548/346.1; 514/396

(58) Field of Classification Search ............... 548/335.1, 548/346.1; 514/396
See application file for complete search history.

(56) References Cited

U.S. PATENT DOCUMENTS
4,544,664 A 10/1985 Karjalainen et al.

FOREIGN PATENT DOCUMENTS
GB 2069481 8/1981

OTHER PUBLICATIONS

Cordi, et al., Synthetic Communications, 1996, 26, 1585-1593.
International Preliminary Report on Patentability for International Application No. PCT/EP2007/061822, May 12, 2009.
International Search Report for International Application No. PCT/EP2007/061822, Mar. 26, 2008.
Official Action issued in European Application No. 07822154.6, Nov. 4, 2009.
Reply to Official Action issued in European Application No. 07822154.6, Feb. 23, 2010.
Turner, et al., J. Org. Chem., 1991, 56, 5739-5740.
Zhang, et al., J. Med. Chem., 1996, 39, 3001-3013.

*Primary Examiner* — Joseph R Kosack
*Assistant Examiner* — Matthew P Coughlin
(74) *Attorney, Agent, or Firm* — Hueschen and Sage

(57) ABSTRACT

The invention provides an improved, highly efficient method for preparing Medetomidine, and its salts, in particular its pharmaceutically acceptable salts. The method utilizes the high reactivity of halogenated imidazoles towards transmetalation with Grignard reagents and the subsequent reaction with 2,3-dimethylbenzaldehyde.

33 Claims, No Drawings

METHOD FOR PREPARING MEDETOMIDINE AND ITS SALTS

FIELD OF THE INVENTION

The present invention concerns an improved, highly efficient method for preparing (±)-5-[1-(2,3-dimethylphenyl)ethyl]-1H-imidazole hydrochloride (international non-proprietary name "medetomidine") and salts, in particular pharmaceutically acceptable salts, thereof.

BACKGROUND ART (±)-5-[1-(2,3-Dimethylphenyl)ethyl]-1H-imidazole hydrochloride having the formula (I) following below is a synthetic α-2-adrenoreceptor agonist with sedative and analgesic properties U.S. Pat. No. 4,544,664 discloses the leading multi-step process for preparing (±)-5-[1-(2,3-dimethylphenyl)ethyl]-1H-imidazole hydrochloride. The process starts with 2,3-dimethylmagnesium bromide, which is prepared from magnesium and 2,3-dimethylbromobenzene, while in a separate step this Grignard reagent is added to 4-imidazolecarboxylic acid methyl ester. The intermediate is hydrogenated in the presence of a palladium on carbon catalyst in hydrochloric acid.

GB 2069481 discloses the preparation of 5-[1-(2,3-dimethylphenyl)ethyl]-1H-imidazole hydrochloride via the intermediate 4-[(2',3'-dimethylphenyl)-ethyl]-N-acetylimidazole or 4-[(2',3'-dimethylphenyl)-ethyl]-N-benzylimidazole. In the processes described therein acetyl and benzyl groups are used as protecting groups of the intermediate products for increasing product yield.

In a further process described in this patent N-(trimethylsilyl)imidazole is used as a starting material, which is reacted with titanium tetrachloride in dry chloroform. In this case as protecting group a trimethylsilyl group is used. The use of a benzyl group as a protecting group is also mentioned therein.

The main disadvantage of the methods described in the above prior art documents is that medetomidine is obtained in low yields.

DISCLOSURE OF THE INVENTION

Technical Problem

The technical problem to be solved by the present invention is to prepare (±)-5-[1-(2,3-dimethylphenyl)ethyl]-1H-imidazole and its salts, especially its pharmaceutically acceptable salts, in higher yields than before.

Technical Solution

Surprisingly, it has been found that the above problem can be solved by using as a starting material 4-iodo-1-trityl-1H-imidazole or a derivative thereof (I)

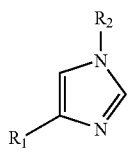
[I]

wherein $R_1$ is halogen, preferably iodine or bromine, and $R_2$ is a suitable protecting group, preferably a trityl group, a benzyl group or a trimethylsilyl group, which is reacted with 2,3-dimethylbezaldehyde (II)

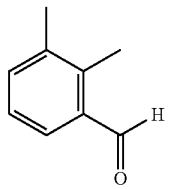
[II]

in order to prepare (2,3-dimethylphenyl)-(3-trityl-3H-imidazol-4-yl) methanol (III):

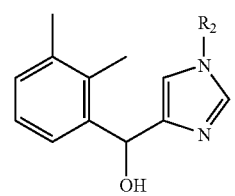
[III]

wherein $R_2$ is defined as before (step a).

Thereafter (2,3-dimethylphenyl)-(3-trityl-3H-imidazol-4-yl)methanol (III) is oxidised with an oxidizing agent, preferably manganese (IV) oxide, to yield (2,3-dimethylphenyl)-(3-trityl-3H-imidazol-4-yl)methanone (IV):

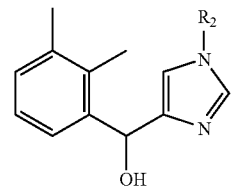
[IV]

wherein $R_2$ is defined as before (step b).

In a further step a compound of formula (V) is formed by a Grignard reaction in which a compound of the above formula (IV) is reacted with a compound of formula: $R_3$MgHal wherein $R_3$ is alkyl and Hal is halogen:

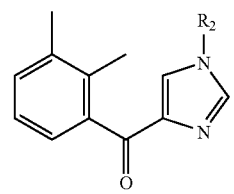
[V]

wherein $R_2$ is defined as before (step c).

The removal of the protecting group can be performed in different ways, and depends on the particular protecting group. Thereafter the compound of formula (V) is treated with an appropriate acidic solution, preferably with a hydrochloric acid solution and 5-[1-(2,3-dimethylphenyl)vinyl]-1H-imidazole (VI) is obtained (step d):

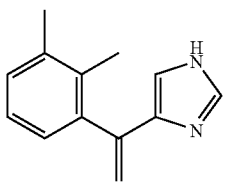

[VI]

Finally, the compound of formula (VI) is hydrogenated in the presence of a suitable catalyst, preferably palladium on carbon or Raney nickel, in an appropriate acidic solution, preferably in hydrochloric acid media (step e), and after crystallization 5-[1-(2,3-dimethylphenyl)ethyl]-1H-imidazole hydrochloride hydrate (VII) is obtained as the desired product (VIII) (step f):

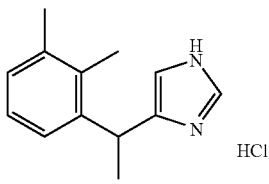

[VIII]

The pharmaceutically acceptable salts of these compounds are also within the scope of the invention.

The compounds of formula (VIII) may be reacted with both organic and inorganic acids. They can thus form many usable acid addition salts, as, for instance, chlorides, bromides, sulfates, nitrates, phosphates, sulfonates, formates, tartrates, maleates, citrates, benzoates, salicylates, ascorbates and the like.

Advantageous Effects

The method of preparation of (±)-5-[1-(2,3-dimethylphenyl)ethyl]-1H-imidazole hydrochloride and other salts, especially pharmaceutically acceptable salts thereof is advantageous in that the above new conditions of the preparation increase the yield of the product.

By using 4-iodo-1-trityl-1H-imidazole or its derivatives as a starting material and by increasing the process steps to 6 steps instead of 4 steps as described in U.S. Pat. No. 4,544,664 surprisingly a substantially higher yield of (±)-5-[1-(2,3-dimethylphenyl)ethyl]-1H-imidazole hydrochloride and its salts, especially its pharmaceutically acceptable salts, can be obtained.

Another advantageous effect that can be mentioned is that by using a trityl group as a protecting group this group can be removed more easily than a benzyl group as used in U.S. Pat. No. 4,544,664. Trityl alcohol, which is obtained in the synthesis process, can be regenerated to trityl chloride, thereby comparatively high costs of the trityl group can be reduced.

The complete process of the present invention is illustrated in the enclosed FIG. 1.

BEST MODE FOR CARRYING OUT THE INVENTION

The present invention will be better understood by reference to the following Examples, which are provided as exemplary of the invention, and not as a limitation.

EXAMPLE 1

Step A

Preparation of (2,3-Dimethylphenyl)-(3-trityl-3H-imidazol-4-yl)methanol

A solution of isopropylmagnesium bromide in tetrahydrofuran (48 mL, 0.046 mol) was added to a stirred solution of 4-iodo-1-trityl-1H-imidazole (19.0 g, 0.046 mol) in dichloromethane (180 mL) at 10 to 15° C. The reaction mixture was allowed to warm to the ambient temperature and was stirred at ambient temperature for 1 hour. The reaction mixture was then cooled to 10-15° C., at which point a solution of 2,3-dimethylbenzaldehyde (6.2 mL, 0.046 mol) in dichloromethane (10 mL) was added, while not exceeding 20 to 25° C. After additional stirring for 1 hour at ambient temperature a 10% aqueous ammonium chloride solution (200 mL) was added to the reaction mixture. The organic layer was separated and washed with an aqueous sodium chloride solution (150 mL), thereafter the organic layer was concentrated to a volume of 40 mL.

A precipitate of (2,3-dimethylphenyl)-(3-trityl-3H-imidazol-4-yl)methanol was obtained upon cooling the distillation residue to 4° C. and it was separated by filtration, then washed with dichloromethane (50 mL).

The intermediate (2,3-dimethylphenyl)-(3-trityl-3H-imidazol-4-yl)methanol was dried at ambient temperature. The yield was 17.4 g (84%) of a white or off-white powder, having a melting temperature of 203.0 to 207.0° C.

EXAMPLE 2

Step b

Preparation of (2,3-dimethylphenyl)-(3-trityl-3H-imidazol-4-yl)methanone 2,3-Dimethylphenyl)-(3-trityl-3H-imidazol-4-yl)methanol (248 g, 0.558 mol) was added to stirred dichloromethane (5000 mL) in a 10-liter glass reactor, fitted with a reflux condenser and a thermometer. Thereafter manganese (IV) oxide (305 g, 3.51 mol) was added to the reaction mixture. The reaction mixture was heated at reflux for 2 hours at 40° C. The precipitate of manganese oxides was separated by filtration; the damp cake on the filter was washed with dichloromethane (700 mL).

The clear filtrate was poured into a 10-liter glass reactor, fitted with a stirrer, a distillation condenser and a thermometer. The reaction mixture was stirred while dichloromethane was distilled off at 40° C. Thereafter 96% ethanol (1000 mL) was added to the reaction mixture and the residual dichloromethane was removed by distillation at 50 to 55° C.

The reaction mixture was stirred and cooled to −1 to −3° C. The precipitate was separated by filtration and washed with cold (0-5° C.) 96% ethanol (200 mL). The yield was 216 g (90.3%) of white crystalline (2,3-dimethylphenyl)-(3-trityl-3H-imidazol-4-yl)methanone, having a melting temperature of 172.5° C. to 174.0° C.

EXAMPLE 3

Step c

Preparation of 1-(2,3-dimethylphenyl)-1-(3-trityl-3H-imidazol-4-yl)ethanol (2,3-Dimethylphenyl)-(3-trityl-3H-imidazol-4-yl)methanone (216 g, 0.488 mol) was added to stirred tetrahydrofuran (3000 mL) in a 6-liter glass reactor fitted with a mechanical stirrer, a thermometer, a dropping funnel and a tube for argon introduction into the reaction mixture.

A methylmagnesium chloride solution in tetrahydrofuran (190 mL, 0.584 mol) was added dropwise to the reaction mixture at 0° C. under an argon atmosphere. The reaction mixture was maintained at 0° C. After addition of a methylmagnesium chloride solution the reaction mixture was warmed to 25° C. over 3.5 hours, at which point 10% aqueous ammonium chloride solution (90 mL) was added to the reaction mixture. The organic layer was separated and washed with saturated sodium chloride solution (700 mL). The organic layer was concentrated in vacuo to 20% of the original volume; the residue was cooled and allowed to crystallize at 0 to 5° C. for 1 hour.

The precipitate was separated by filtration and washed with cold (0 to 5° C.) tetrahydrofuran (360 mL).

The obtained intermediate 1-(2,3-dimethylphenyl)-1-(3-trityl-3H-imidazol-4-yl)ethanol was dried at a reduced pressure at 40-50° C.

The yield was 214.2 g (97.5%) of white crystalline 1-(2,3-dimethylphenyl)-1-(3-trityl-3H-imidazol-4-yl)ethanol, having a melting temperature of 226.5° C. to 228.5° C.

EXAMPLE 4

Step d

Preparation of 5-[1-(2,3-dimethylphenyl)vinyl]-1H-imidazole 1-(2,3-dimethylphenyl)-1-(3-trityl-3H-imidazol-4-yl) ethanol (212 g, 0.462 mol) was added to hydrochloric acid (2120 mL) in a 6-liter glass reactor, fitted with a reflux condenser and a thermometer. The reaction mixture was heated to reflux (99-101° C.) and maintained at 99-101° C. for 2 hours, at which point it was cooled to 17-23° C. The precipitate of triphenylcarbinol was separated by filtration; the damp cake on the filter was washed with water (700 mL).

Water (2,5 L) was added to the filtrate, and the mixture was poured into a 10-liter glass reactor. The stirred reaction mixture was cooled to 0° C., at which point 10% of an aqueous sodium hydroxide solution (2120 mL) was added to the reaction mixture. The reaction mixture was heated to 20-25° C. and stirred for 60-90 minutes.

The suspension was filtered; the product cake on filter was washed with water (700 mL).

The obtained intermediate 5-[1-(2,3-dimethylphenyl)vinyl]-1H-imidazole was dried at ambient conditions for 10-12 hours and at 50 to 60° C. under reduced pressure for 8-10 hours. The yield was 82.2 g (89.2%) of white crystalline 5-[1-(2,3-dimethylphenyl)vinyl]-1H-imidazole, having a melting temperature of 145.7° C. to 146.6° C.

EXAMPLE 5

Step e

Preparation of 5-[1-(2,3-dimethylphenyl)ethyl]-1H-imidazole hydrochloride hydrate 5-[1-(2,3-dimethylphenyl)vinyl]-1H-imidazole (80.0 g, 0.406 mol) and methanol (800 mL) were mixed in a 2-liter beaker. The reaction mixture was poured into a stirred laboratory autoclave. Palladium catalyst (1.9 g of 5% Pd/C) was weighed and immediately suspended in water (25 mL). The suspension was poured into the autoclave. The autoclave was closed and flushed 2 times with hydrogen to $0.21 \times 10^6$ Pa. The hydrogen was supplied to autoclave to $0.21 \times 10^6$ Pa. The reaction mixture was stirred and warmed to 44-46° C. over 20-25 minutes. At the end of the hydrogenation, the hydrogen absorption ceased, and the pressure in the autoclave remained constant. The typical hydrogenation time was 1.5 hours. After hydrogenation the autoclave was flushed with nitrogen, the reaction mixture was filtered to remove the catalyst. The autoclave and the catalyst were washed with methanol (200 mL).

The solvent was removed by distillation at a reduced pressure. Hydrochloric acid (4 M, 350 mL) was added to the distillation residue at 38 to 42° C. At first the reaction mixture was stirred without cooling for 30 minutes; then the reaction mixture was cooled to −5 to −10 ° C. for 2 to 2.5 hours.

The precipitates were separated by filtration. The obtained intermediate 5-[1-(2,3-dimethylphenyl)ethyl]-1H-imidazole hydrochloride hydrate was dried at ambient temperature for 15 to 17 hours. The yield was 94.8 g (89-98%) of an off-white powder.

EXAMPLE 6

Step f

Preparation of (±)-5-[1-(2,3-dimethylphenyl)ethyl]-1H-imidazole hydrochloride

5-[1-(2,3-dimethylphenyl)ethyl]-1H-imidazole hydrochloride hydrate (89 g), acetone (855 mL) and water (34 mL) were mixed in a 2-liter flask, fitted with a thermometer and a reflux condenser. The reaction mixture was heated to 56-58° C. for 15 minutes, at which point it was filtered. The filtrate was at first cooled to 20-30° C. over 1 to 1.5 hours, and then it was cooled to 0 to −10)° C. for 2.5 to 3.5 hours.

The precipitates were separated by filtration and the product cake on the filter was washed with cooled (0-5° C.) acetone (80-100 mL). The (±)-5-[1-(2,3-dimethylphenyl) ethyl]-1H-imidazole hydrochloride was dried at a reduced pressure for 2-3 hours. The yield was 78.4 g (98.5%) of colorless crystalline powder, melting at 168° C. to 172° C.

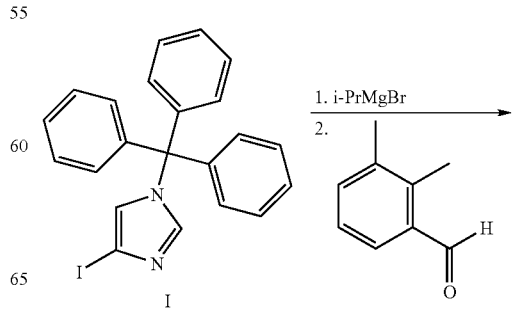

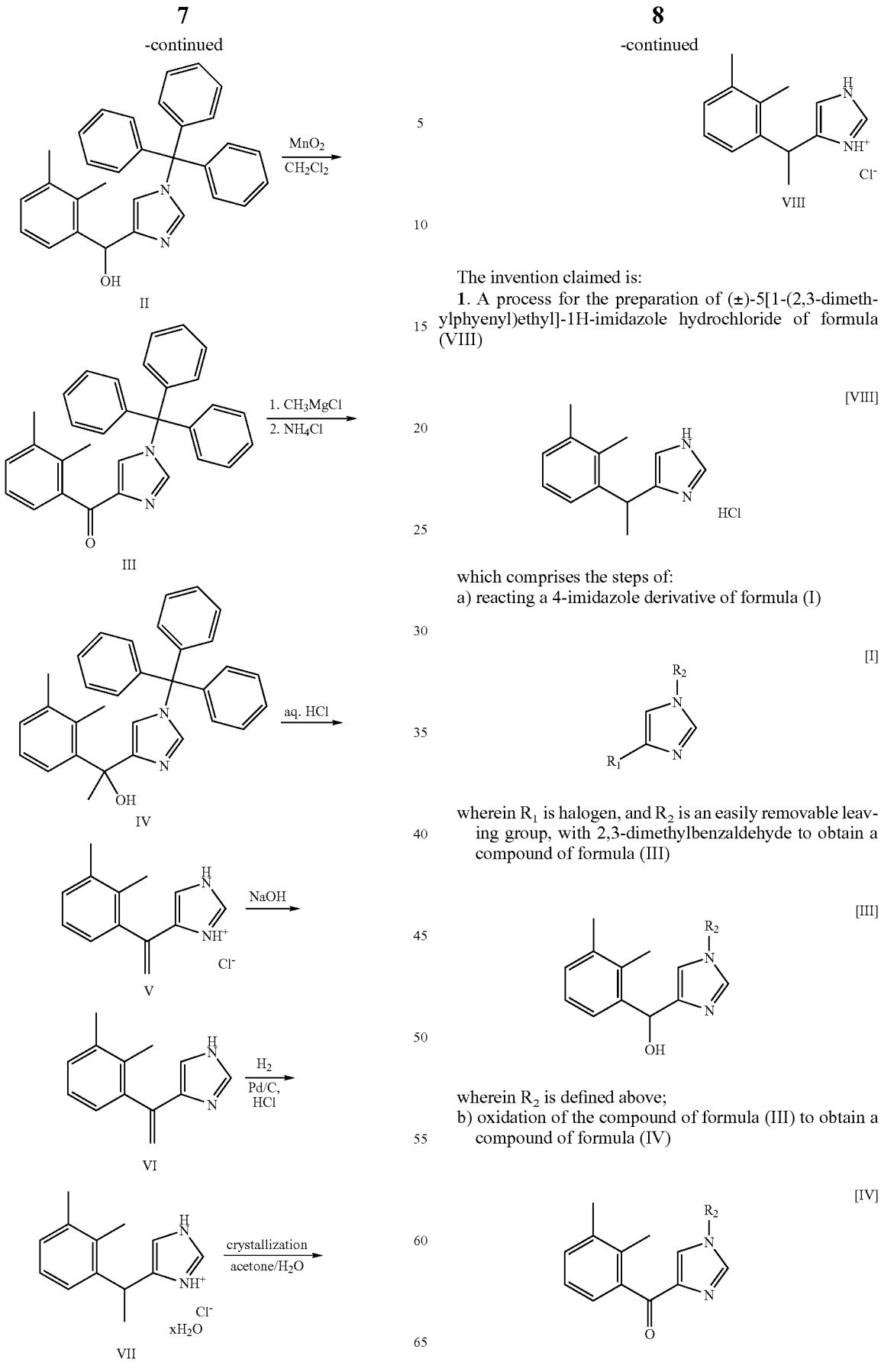

c) reaction of the compound of formula (IV) with a Grignard reagent R₃MgHal, wherein R₃ is alkyl and Hal is halogen, to obtain a compound of formula (V)

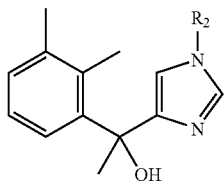
[V]

wherein R₂ is defined above;
d) removing the group R₂ from the compound of formula (V) to obtain the compound of formula (VI)

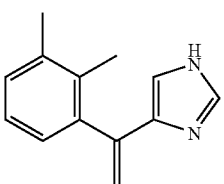
[VI]

e) hydrogenation of the compound of formula (VI) to obtain the compound of formula (VII)

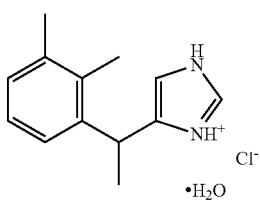
[VII]

f) crystallization of the compound of formula (VII) to obtain the compound of formula (VIII).

2. The process of claim 1, wherein R₁ is Br or I.
3. The process of claim 1, wherein R₁ is I.
4. The process of claim 1, wherein, in the reaction of step a), R₂ is an easily removable leaving group selected from benzyl, trimethylsilyl and trityl.
5. The process of claim 2, wherein R₂ is a trityl group.
6. The process of claim 1, wherein, in the reaction of step a), R₁ is I and R₂ is a trityl group, and the compound of formula (I) is 4-iodo-1-trityl-1H-imidazole.
7. The process of claim 1, wherein the reaction in step a) is carried out in the presence of a Grignard reagent selected from the group consisting of alkylmagnesium halides.
8. The process of claim 7, wherein the alkylmagnesium halide is isopropylmagnesium bromide.
9. The process of claim 1, wherein the reaction of step a) is carried out in the presence of a solvent selected form the group consisting of halogenated solvents.
10. The process of claim 9, wherein the halogenated solvent is dichloromethane.
11. The process of claim 1, wherein the oxidation reaction of step b) is carried out with a suitable oxidant.
12. The process of claim 11, wherein the suitable oxidant is manganese (IV) oxide.
13. The process of claim 1, wherein the reaction of step b) is carried out at a temperature from 20° C. to 80° C.
14. The process of claim 13, wherein the reaction of step b) is carried out at a temperature from 30° C. to 50° C.
15. The process of claim 13, wherein the reaction of step b) is carried out at a temperature from 35° C. to 45° C.
16. The process of claim 1, wherein, in the reaction of step c) the Grignard reagent is selected form the group consisting of alkylmagnesium halides.
17. The process of claim 16, wherein, in the reaction of step c) the alkylmagnesium halide is methylmagnesium chloride.
18. The process of claim 1, wherein, in the reaction of step c) the solvent is selected from the group consisting of ethers.
19. The process of claim 18, wherein the ether is tetrahydrofuran.
20. The process of claim 1, wherein the reaction phase of step d) is carried out at a temperature from 30° C. to 150° C.
21. The process of claim 20, wherein the reaction phase of step d) is carried out at a temperature from 80° C. to 120° C.
22. The process of claim 20, wherein the reaction phase of step d) is carried out at a temperature from 95° C. to 105° C.
23. The process of claim 1, wherein the reaction medium of step d) is selected from the group consisting of strong acids.
24. The process of claim 23, wherein the strong acid is hydrochloric acid.
25. The process of claim 1, wherein the hydrogenation of step e) is carried out with a suitable catalyst.
26. The process of claim 25, wherein the suitable catalyst is palladium on carbon.
27. The process of claim 1, wherein the solvent of step e) is selected from appropriate acid solutions.
28. The process of claim 27, wherein the acid solution is aqueous hydrochloric acid.
29. The process of claim 1, wherein the reaction of step f) is carried out at a temperature of from 30° C. to 120° C.
30. The process of claim 29, wherein the reaction of step f) is carried out at a temperature of from 40° C. to 80° C.
31. The process of claim 29, wherein the reaction of step f) is carried out at a temperature of from 55° C. to 60° C.
32. The process of claim 1, wherein the solvent for crystallization is selected from the group consisting of ketones.
33. The process of claim 32, wherein the solvent is acetone.

* * * * *